(12) United States Patent
Ågerup

(10) Patent No.: US 7,156,837 B2
(45) Date of Patent: Jan. 2, 2007

(54) ARRANGEMENT AND A METHOD FOR INTERACTING WITH AN INTERNAL BODY ORGAN

(75) Inventor: Bengt Ågerup, Paris (FR)

(73) Assignee: Q Med AB, Uppsala (SE)

( * ) Notice: Subject to any disclaimer, the term of this patent is extended or adjusted under 35 U.S.C. 154(b) by 695 days.

(21) Appl. No.: 10/312,673

(22) PCT Filed: Jul. 4, 2001

(86) PCT No.: PCT/SE01/01538

§ 371 (c)(1),
(2), (4) Date: Dec. 31, 2002

(87) PCT Pub. No.: WO02/09802

PCT Pub. Date: Feb. 7, 2002

(65) Prior Publication Data

US 2003/0176840 A1  Sep. 18, 2003

(30) Foreign Application Priority Data

Jul. 27, 2000 (SE) .................................... 0002778

(51) Int. Cl.
*A61M 31/00* (2006.01)
(52) U.S. Cl. ...................... 604/514; 604/264; 604/104; 606/191
(58) Field of Classification Search ................ 604/500, 604/44, 506, 515, 115, 117, 96.01, 264, 164.01, 604/164.04, 272–274, 523, 528, 533, 104, 604/514; 600/29, 30, 464, 227, 228, 234; 606/27–32, 41, 44, 191; 607/96–107, 120, 607/138, 115, 116
See application file for complete search history.

(56) References Cited

U.S. PATENT DOCUMENTS

| | | | |
|---|---|---|---|
| 4,909,789 A | | 3/1990 | Taguchi et al. |
| 5,053,041 A | | 10/1991 | Ansari et al. |
| 5,323,765 A | | 6/1994 | Brown |
| 5,370,675 A | | 12/1994 | Edwards et al. |
| 5,419,777 A | | 5/1995 | Hofling |
| 5,509,900 A | * | 4/1996 | Kirkman ..................... 604/104 |
| 5,512,037 A | | 4/1996 | Russell et al. |
| 5,690,606 A | | 11/1997 | Slotman |
| 6,009,877 A | * | 1/2000 | Edwards ..................... 128/898 |
| 6,425,887 B1 | * | 7/2002 | McGuckin et al. ......... 604/272 |

(Continued)

FOREIGN PATENT DOCUMENTS

FR   2 757 406   6/1998

(Continued)

OTHER PUBLICATIONS

International Search Report.

(Continued)

*Primary Examiner*—Cris L. Rodriguez
(74) *Attorney, Agent, or Firm*—Harness, Dickey, & Pierce (57) ABSTRACT

Example embodiments of the present invention relate to an arrangement and a method for interacting with an internal body organ. The arrangement may include a sheath in which at least two elongate structural elements are inserted. The structural elements may each have a proximal end and a distal end. The sheath may have a proximal end and a distal end, said distal end being open. When the structural elements are displaced relative to the sheath, they may extend through the open distal end of the sheath and at least partly in the transverse direction away from the sheath for distending and/or expanding interaction between the distal end of each structural element and a body organ.

43 Claims, 5 Drawing Sheets

U.S. PATENT DOCUMENTS

| | | | |
|---|---|---|---|
| 6,645,201 B1 * | 11/2003 | Utley et al. | 606/41 |
| 6,652,515 B1 * | 11/2003 | Maguire et al. | 606/41 |
| 6,939,322 B1 * | 9/2005 | Crank et al. | 604/117 |
| 2003/0024538 A1 * | 2/2003 | Edwards et al. | 128/898 |
| 2005/0245926 A1 * | 11/2005 | Edwards et al. | 606/41 |

FOREIGN PATENT DOCUMENTS

| | | |
|---|---|---|
| FR | 2757406 | 6/1998 |
| JP | 9-75353 | 3/1997 |
| JP | 9-509865 | 10/1997 |
| WO | 0066499 | 11/2000 |

OTHER PUBLICATIONS

Japanese Patent Office Communication dated Aug. 30, 2005 (in English) for Japanese Application No. 2002-515353.

Australian Office Action dated Oct. 28, 2004.

* cited by examiner

ARRANGEMENT AND A METHOD FOR INTERACTING WITH AN INTERNAL BODY ORGAN

TECHNICAL FIELD

The present invention relates to an arrangement to be passed through a body cavity for interacting with an internal body organ and a method for interacting with an internal body organ.

TECHNICAL BACKGROUND

In the wide field of medicine it is often of great importance for a surgeon to be able to interact with a human organ through a body cavity. The reasons for interacting with the organ may be to inject an agent into the organ, to manipulate the organ, to obtain information related to the organ by sampling, by viewing it, or by other means of sensing, etc.

The organ or the tissue to be accessed is often located in a narrow space which is difficult to reach. If, additionally, the organ is located deep inside the human body, special tools or pieces of equipment are required. Because of these access limiting conditions, it is often preferred to use an elongate structural element for interacting with the organ.

However, in order to accurately interact with the organ, different types of supplemental aid are used in the prior art. These supplemental aids are often complex and expensive. They may involve identification of anatomic points by means of special complex machinery. Furthermore, the elongate structural element often needs some sort of supporting machinery.

The prior art devices may be quite difficult to handle correctly and efficiently, and because of their complexity they often require highly trained staff. It is not unusual that the prior art devices require at least two people for carrying out the accessing procedure.

Furthermore, the prior art devices do not only involve problems for the persons carrying out the interacting procedure, they often also involve problems for the person who is subject to the interacting procedure. Because of all the extra equipment, the procedure may be quite an unpleasant, traumatic and stressful experience.

SUMMARY OF THE INVENTION

One object of the present invention is to provide an arrangement and a method for interacting with an internal body organ, which are simple and inexpensive.

Another object of the invention is to achieve an improved procedure for interacting which is less traumatic for the person subjected to said procedure.

Yet another object of the invention is to achieve an arrangement which is versatile and flexible as regards the use thereof.

These and other objects which will become apparent in the following are achieved by means of an arrangement and a method having the features stated in the appended claims.

Thus, according to one aspect of the present invention an arrangement to be passed through a body cavity for interacting with an internal body organ is provided. The arrangement comprises an elongate sheath having at least one interior passage. The sheath has a proximal end and a distal end, said distal end being open and in communication with said at least one passage. The arrangement further comprises at least two elongate structural elements, each structural element having a proximal end and a distal end, wherein the structural elements are inserted in said at least one passage so that at least a distal portion of each element extends therethrough in the longitudinal direction of the sheath. The structural elements are arranged to be displaced relative to the sheath from a first position, in which the distal end of each structural element is located inside said at least one passage and in which the arrangement is intended to be passed through a body cavity, to a second position, in which a distal portion of each structural element extends through the open distal end of the sheath and at least partly in the transverse direction away from the sheath for distending and/or expanding interaction between the distal end of each structural element and a body organ approached by the arrangement through a body cavity.

As will later be explained, this distending and/or expanding interaction is particularly suitable for injection procedures.

According to another aspect of the invention a method is provided for interacting with an internal body organ through a body cavity. The method comprises the steps of:

providing an elongate tubular sheath having at least one interior passage, said sheath having a proximal end and a distal end, said distal end being open and in communication with said at least one passage;

introducing at least two elongate structural elements in said at least one passage so that at least a distal portion of each element extends through said at least one passage in the longitudinal direction of the sheath, each structural element having a distal end and a proximal end, and so that the distal end of each structural element is located inside said at least one passage;

inserting the sheath and the structural elements into the body cavity;

displacing the structural elements relative to the sheath through said open distal end of the sheath so as to expose the distal ends of each structural element; and bringing the distal end of each structural element in the transverse direction of and away from the sheath so that the distal end of each structural element interacts with the body organ in a distending and/or expanding manner.

The invention is thus based on the understanding that it is possible to interact efficiently with an internal body organ even with a limited number of supplemental aids. The invention is further based on the insight that the organ may be effectively protected from unnecessary stress by limiting the radial extension of the elongate structural elements during their advancement through the body cavity to the internal organ. It is to be understood that in this disclosure the term "organ" may be interpreted as the organ per se, as well as an organ cavity or body cavity. It is also to be understood that in this disclosure the term "body cavity" may be interpreted as a natural cavity of the body, as well as cavity produced artificially, e.g. by means of a surgical instruments.

It should also be understood that in this disclosure the terms "distal" and "proximal" are from an operator point of view and not from a patient point of view.

An advantageous feature of the present invention is that that portion of each structural element which extends through the open distal end of the sheath is beyond the sheath, i.e. the structural elements protrude through an imagined end surface of the sheath. This means that the distal ends of each structural element can, freely and undisturbed by the sheath, interact with a body organ so as to distend and/or expand it.

The person skilled in the art realises that each elongate structural element can be inserted and passed through a respective sheath passage or channel to the distal end of the sheath for achieving the distending and/or expanding effect. However, a simpler construction is a tubular sheath having a lumen or bore, wherein the elongate structural elements are inserted in one and the same "passage". In the following the emphasis of this description will be on such a tubular sheath having a lumen.

The tubular sheath effectively protects the body organ and any other tissue passed by the elongate structural elements when introduced in the sheath, and also serves as a limiter or restrictor for the structural elements by keeping their ends from deviating sideways. As the distal ends of the elongate structural elements are displaced relative to the sheath and extend through the opening thereof, said distal ends are allowed to deflect radially so as to interact with the organ.

As has been mentioned, when the elongate structural elements exit the sheath to interact with the body organ, they all extend through the open tip or distal end of the sheath. That is, they all extend through, preferably, one and the same opening, which has a relatively large diameter compared to the diameter of each individual elongate structural element. However, the sheath has suitably such a small diameter as permitted by the thickness of the elongate structural elements, in order to keep the transverse dimension of the arrangement small. The opening is, preferably, only defined by the wall of the sheath.

An arrangement according to the present invention comprises at least two elongate structural elements. Depending on the specific application the number may vary. For instance, in some cases 12 structural elements may conveniently be used, in others it may be preferable to use less, such as four.

The extension of the structural elements through the open distal end of the sheath and in the transverse direction away from the sheath means that the mutual distance between the distal ends of the structural elements is enabled to be larger in the spread second position, than in the cased first position inside the sheath. There are of course a number of possibilities for achieving this, wherein only a few will be disclosed hereinafter.

The elongate structural elements are preferably arranged to be angularly deflected in an outward radial direction into said second position. In said second position they are preferably circumferentially spaced. One way to achieve such an angular deflection is to arrange the sheath for reception of the elongate structural elements from the side of the sheath wall through lateral apertures into the lumen, as will later be described in more detail. The structural elements will be forced to bend inside the sheath and thus become biased, striving for outward radial deflection. Another way is to use "naturally" biased elongate structural elements, which are advanced from the proximal end of the sheath, e.g. through apertures, and distally straight through the lumen of the sheath. A third option is to have the proximal ends of the elongate structural elements connected to a rotating head, wherein the distal ends of the elongate structural elements can be caused to a radial change of position by rotating the head.

Thus, according to a preferred embodiment of the present invention, the sheath wall is provided with at least one lateral aperture in communication with said lumen, for allowing introduction of said elongate structural elements into the lumen of the sheath. Preferably, there is one aperture for each structural element to be introduced. Thus, the elongate structural elements are introduced in the sheath from the side. Because of this lateral introduction and the small diameter of the sheath, the elongate structural elements will be somewhat bent as they are bounded or restricted by the sheath wall. Consequently, they are mechanically biased or pre-tensioned, and as a distal end of an elongate structural element exits the opening at the tip or distal end of the sheath, it will deflect or spring out radially.

Suitably, the lateral apertures are slot-shaped with a transverse dimension substantially corresponding to the transverse dimension of the structural element to be introduced. The cross section of the structural elements is suitably essentially circular, in which case the width of each aperture substantially corresponds to the diameter of the respective structural element. The extension of a slot-shaped aperture would generally be in the axial direction of the sheath wall. One advantage of such an aperture is that it functions well as a means of guiding for a structural element. Another advantage is that it contributes in defining the limits for the displacement of the sheath. If the elongate structural elements are kept in a fixed position, the sheath can only be moved a distance that is equal to the length of the slot. As an elongate structural element bars against the respective ends of the slot, the sheath will be prevented from being further displaced in that direction.

The lateral apertures, preferably slots, are in one advantageous embodiment evenly spaced around the circumference of the sheath wall. This, together with other dimensional-features of the present invention, has the effect that the elongate structural elements will be received crossed in the lumen. When the sheath releases the structural elements through its open distal end, the structural elements will come out intersecting, i.e. crossing, each other. Thus, in such an embodiment the structural elements will extend "diagonally" and essentially cut across the central longitudinal axis of the sheath.

The aperture, preferably a slot, also serves as a stop for the elongate structural element, which will abut against the distal end of the slot when the distal end of the structural element is in said second position outside the sheath. This means that it is possible to accurately anticipate the second position of the distal end of the elongate structure already when it is in the first position, i.e. inside the sheath. If the slot is made shorter or is partly clogged or packed, then the structural elements will be "shorter" as well, i.e. they will not extend as far distally as with a longer or an unclogged slot. It is also possible to split one slot into two slots arranged in series, one after the other. This enables, for instance, two elongate structural elements to be placed generally in parallel, one slightly above the other.

Even though the sheath has a tubular shape, it may have alternative cross sections. Thus, it does not necessarily have to he circular, but can be adapted in accordance with the desired application. For instance, the sheath may have an elliptical cross section for elliptical spaces, such as the vocal cords. Also, the cross section can be varied along the extension of the sheath.

In order to, inter alia, provide stability, the arrangement is preferably provided with a sheath holder. As the name reveals, it functions to hold the sheath. Apart from that, it will preferably also function to guide the sheath in the longitudinal centre axis direction of the sheath. This enables the relative displacement of the distal ends of the structural elements from said first position to said second position, and vice versa. Accordingly, the elongate structural elements may be kept in a fixed position while the sheath is retracted, thereby exposing the structural elements and allowing a deflection similar to that of the opening of an umbrella.

The means for holding and guiding the sheath is suitably a hole in the sheath holder. The hole conveniently has a transverse dimension which substantially corresponds to the transverse dimension of the sheath, wherein at least a partial extension of the sheath is allowed to be passed through said hole. The hole may have alternative shapes and may be provided with rails or other means for facilitating the handling of the sheath.

In order to ensure that the sheath is not advanced too much, a proximal stop is preferably provided on the outside of the sheath wall at a proximal portion thereof. This stop interacts with a portion of the sheath holder, thereby limiting distal advancement.

The sheath may also, or alternatively, have a stopping means provided on the outside of the sheath wall, preferably, at a distal portion thereof. This stopping means interacts with a portion of the sheath holder, thereby limiting proximal retraction of the sheath. Such a stopping means may for example be shaped as a barb that allows the sheath to be passed through the hole of the sheath holder, but impedes the sheath from being accidentally removed.

Additionally, further use may be made of the sheath holder by using it to guide and align the elongate structural elements. For this purpose the sheath holder is suitably provided with some sort of guiding means, such as channels, one for each structural element. The transverse dimension of such a channel should substantially correspond to the transverse dimension of the structural element. The channels are preferably straight.

Thus, if the sheath is provided with a lateral aperture, an elongate structural element may extend from above the sheath holder, through a channel in the sheath holder, and through the lateral aperture into the lumen. When an elongate structural element is in said second position, the structural element further extends out through the opening at the tip of the sheath.

The elongate structural elements may be arranged in accordance with which body organ or cavity that is to be accessed. For instance, the elongate structural elements are suitably inserted at a certain angle (e.g. between 8°–20°) when one wishes to access the rectum, and at another angle when one wishes to access the urethra. Similar considerations may have to be taken if the procedure is to be carried out on a child instead of on an adult. Accordingly, the channels of the sheath holder may be given an angle of inclination relative the centre longitudinal axis of the tubular sheath that is chosen in accordance with the particular body organ to be accessed.

By configuring the channels with an elongate slit-like cross section or a "sliced" bore, the structural elements can be arranged at different angles of inclination from one time to another. This is practical when the invention is used as a reusable product. The arrangement may naturally be in either the form of a disposable or a reusable product. The angles of the structural elements may, e.g., be adjusted by means of a screwing arrangement.

The channels are suitably located radially externally of the hole for guiding the sheath, and are preferably evenly spaced. However, unevenly spaced channels or asymmetrical configurations are also possible.

The sheath holder may of course have many alternative shapes. Suitably, it is designed to form some sort of handle for facilitating gripping and the subsequent manipulation of the arrangement components.

The present invention has been found very advantageous in connection with injection procedures. Cosmetic and therapeutic treatments are often carried out by injecting an agent or a substance into an organ or tissue, by means of elongate injection needles. Thus, the invention could be used for injections into different, often narrow, areas such as the urethra, the rectum, some arteries and veins, the oesophagus, the external meatus of the ear, the nasal meatuses, the uterus, the vocal cords, some joints, under the skin, etc.

The invention has been found particularly suitable for treating female urine incontinence by injection of a bulking agent or substance. It is generally quite difficult to perforate or pierce the flabby mucous membrane of the urethra. It can be compared to the threading of a worm on a fish hook. The mucous membrane is therefore often required to be smoothed out and stretched so as to facilitate the insertion of the injection needle. Commonly, a balloon which will be filled with a fluid is used for this purpose. The present invention, however, needs no supplementary aid for this purpose. Said at least two elongate structural elements, in this case injection needles or cannulae, are arranged to angularly deflect as their distal ends are passed through the opening in the sheath. The bare distal ends of the needles will thus come to abut the mucous member and, since they are at least two, will co-operate so as to stretch or distend the mucous member. The needles are then caused to puncture the mucous member.

The proximal end of the sheath is preferably open and the lumen of the sheath thus extends between the open proximal end and the open distal end of the sheath. The transverse dimension of the lumen may vary along its length. The use of an arrangement having an open proximal end is particularly advantageous in the case of urine incontinence treatment. In such a treatment, the sheath would be advanced up the urethra until urine starts to drip or flow through the lumen and is detected at the open proximal end. Having found the location where leakage begins, a bulking agent may be injected by means of the injection needles, as will later be described. The advantage of having an open proximal end is that once detection is established, the arrangement is already in the right spot for injection. With prior art arrangements it is often necessary to retract the arrangement to an "estimated" position with the aid of graduation marks.

As mentioned, the present invention is particularly well suited for treatment of urine incontinence. Such a treatment includes the steps of distally advancing the sheath until fluid, i.e. urine in this case, is detected. During this advancement the distal ends of the injection needles (elongate structural elements) may be in a fixed position relative to the sheath and enclosed by the same. Upon detection of fluid the sheath, and suitably the injection needles, may be partially retracted if necessary so that the distal end or the tip of the sheath is aligned with the leakage location of the bladderneck. Then the injection needles are exposed, preferably by having retracted the sheath alone, allowing the distal ends of the injection needles to deviate sideways so as to get into contact with the body tissue. The needles will thus press radially against the tissue surface to be accessed with a force which, inter alia, is determined by 1) the properties of the needles, 2) the distance that the sheath has been retracted, and 3) the angle of the needles in the sheath holder. A wide urethra may require a larger force, while a narrow urethra needs some caution and a smaller force.

Since at least two injection needles are used the body tissue will be distended, thereby facilitating the actual injection. The injection is preferably performed by doing a single reciprocating motion back and forth with each injection needle. The length of such a motion should be small, and just large enough for the needles to penetrate to the correct tissue depth. This depth may depend on the condition of the mucous member and the therapeutic purpose of the procedure.

A great advantage of the present invention is that multiple injections may be carried out simultaneously at different tissue points. After such an injection, a new multiple injection may be performed by moving the needles. This is preferably achieved by covering the needles with the sheath, displacing the whole assembly to a new location and then exposing the needles again. Since the needles are exposed through an opening in the distal end of the sheath, the needles are relatively easily manipulated. The sheath will not be in the way or take up excessive space at the injection site, as could be the case if the needles would have exited through lateral openings in the wall. The present invention makes it possible to successfully perform superficial injections. Furthermore, the relatively large diameter of a sheath would, in case of lateral injection, keep the cavity where the injection takes place expanded. The cavity would remain expanded even after the arrangement is removed. Since the needles in the present invention protrude through and beyond the open distal end of the sheath during the injection procedure, the sheath will be well behind the injection site and will not have the negative effect mentioned above.

As has been mentioned previously, in this disclosure the term "body cavity" includes an artificially accomplished cavity. Thus, the present invention can be used for injecting a substance, e.g. cells, under the skin. In such an injection procedure, a small hole is made through the skin with e.g. a scalpel. Thereafter, an instrument is inserted in said hole and used to make a thin "two-dimensional" cavity with small depth under the skin. The cavity extends generally in a plane parallel to the skin. Then, the arrangement according to the present invention is introduced and the injection needles are, in said second position, spread in one and the same plane, thereby making it possible to inject the substance in a layer under skin, in a way that is similar to a sowing procedure. Apart from the advantages of safe handling of the needles, this procedure, i.a., also achieves good contact between the injected substance and blood.

The present invention may of course be used in other applications as well, in which a body organ is to be accessed by means of elongate structural elements. Such structural elements may, e.g., include information transfer means, such as sensors for chemical probing or light guides, or means for taking specimens or samples, etc.

The inventive concept of spreading the elongate structural elements beyond the sheath may be accomplished in different manners. However, they all have in common that the elongate structural elements are displaced in relation to the sheath. Obviously, one way to do this is to advance the elongate structural elements through the sheath while the sheath is kept in a fixed position. An alternative which in some cases, e.g. in injection procedures, such as treatment of urine incontinence, may be more preferable, is to keep the elongate structural elements fixed while the sheath is retracted proximally so as to expose the distal ends of the structural elements. In such a case a previously described sheath holder is suitable to use. The sheath holder would preferably be arranged for fixing the elongate structural elements or injection needles relative to the sheath holder when the sheath is retracted. A great advantage of this procedure is that the injection needles are not lead forward in relation to the tissue when they are deflected. Thus, no unintentional penetration of the tissue will occur. The expansion of the body cavity and the distending of the tissue will be more controlled. A third way is the combination of the motions in the first two alternatives, i.e. to advance the elongate structural elements while the sheath is retracted.

The flaring or the increasing of the relative distance between the distal ends of the structural elements is suitably commenced simultaneously with the exposure of the distal ends of the structural elements, i.e. as they exit the opening. In those cases when the elongate structural elements are in some way pre-stressed, said flaring will occur automatically as the wall of the sheath no longer holds them back.

Another advantage of the present invention is that, due to the relatively uncomplicated configuration, the arrangement provides excellent transmission of force, as regards the action of the elongate structural elements. This is particularly useful for distending and/or expanding body tissue as previously described.

The elongate structural elements used in the present invention are preferably self-springing or resilient, and at least a portion thereof has a certain degree of flexibility. This is particularly suitable in the embodiment with injection needles.

The sheath and the sheath holder of the present invention are suitably manufactured by injection moulding of for example plastic material, such as polypropylene, polyethylene or any other material which serves the purpose of the invention. The material should be shape permanent and the sheath material should permit sterilisation, e.g. by means of autoclave or radiation treatment.

It should be obvious from the foregoing that the present invention provides a simple and inexpensive product which is manageable by one person.

DETAILED DESCRIPTION OF THE DRAWINGS

Figure 1A:
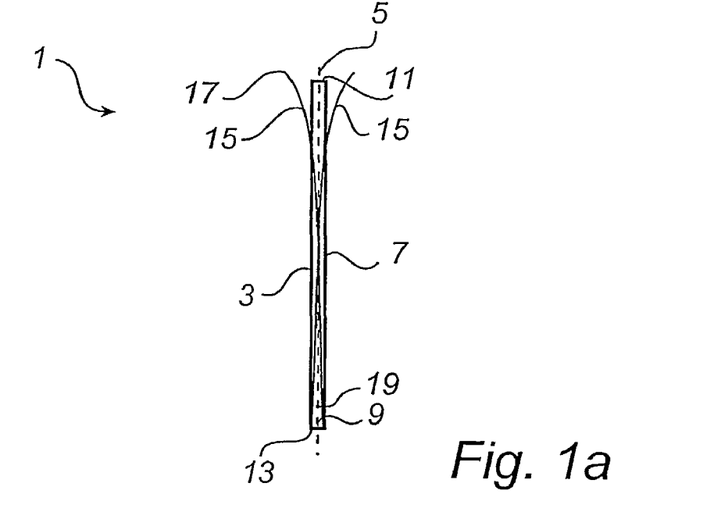
FIGS. 1a and 1b illustrate schematically the principle of the present invention.
Figure 1B:
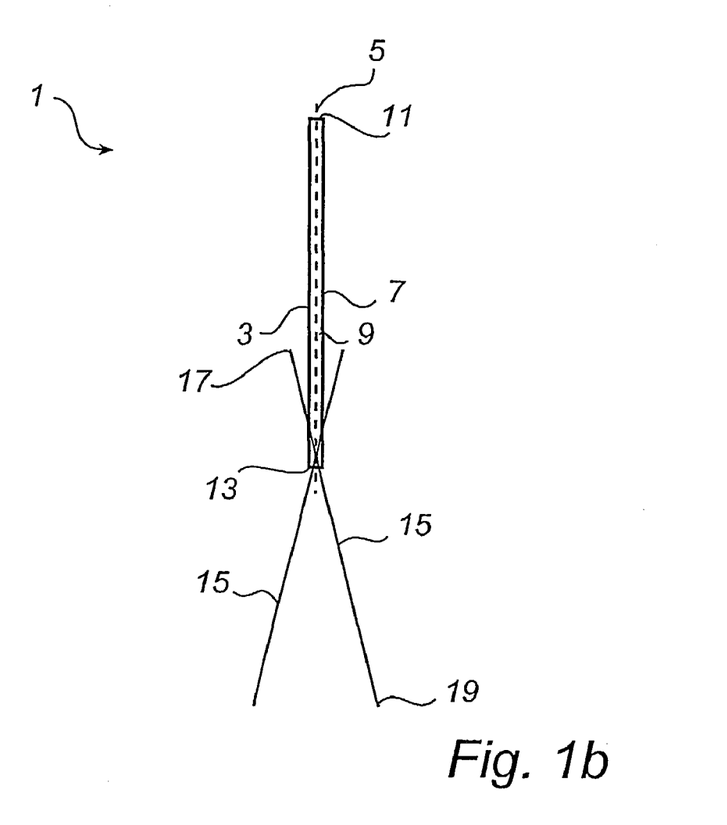

FIGS. 1a and 1b show schematically the principle of the present invention. Accordingly, in FIG. 1a an arrangement 1 to be passed through a body cavity for interacting with an internal body organ is shown. The arrangement 1 comprises a tubular sheath 3, which has a geometrical central longitudinal axis 5 and a wall 7. The wall 7 defines an interior lumen 9. The sheath 3 has a proximal end 11 and a distal end 13, said distal end 13 being open. The arrangement also comprises two elongate structural elements 15 having a generally circular cross section taken perpendicularly to the longitudinal elongation of the structural elements 15. Each structural element 15 has a proximal end 17 and a distal end 19. The structural elements 15 are received by the sheath 3 into the lumen 9 through elongate lateral apertures (not shown) in the wall 7, the apertures extending in the longitudinal direction of the wall 7. As can be seen in FIG. 1a more than half the length of each structural element 15 is covered by the sheath 3. While the proximal end 17 of each structural element 15 is still free, the distal end 19 thereof is hidden inside the sheath 3 and is located near the open distal end 13 of the sheath 3. It should also be noted that, because of the lateral insertion through the apertures and the limited diameter of the sheath 3, the elongate structural elements 15 cross each other.

In FIG. 1b, the sheath 3 has been displaced relative to the elongate structural elements 15, e.g. by retracting the sheath 3 proximally in the direction of its longitudinal axis 5, while keeping the structural elements 15 in a fixed position. As can be seen, the effect thereof is that the structural elements 15 extend through the open distal end 13 of the sheath 3. Being exposed the structural elements 15, in particular their distal ends 19, are now enabled to be deflected outwardly in a radial direction away from the central longitudinal axis 5 of the sheath 3, into the shown position. It may be noted that in this position, more than half the length of each elongate structural element 15 is uncovered, and that the structural elements 15 abut the distal end of the wall 7.

Figure 2A:
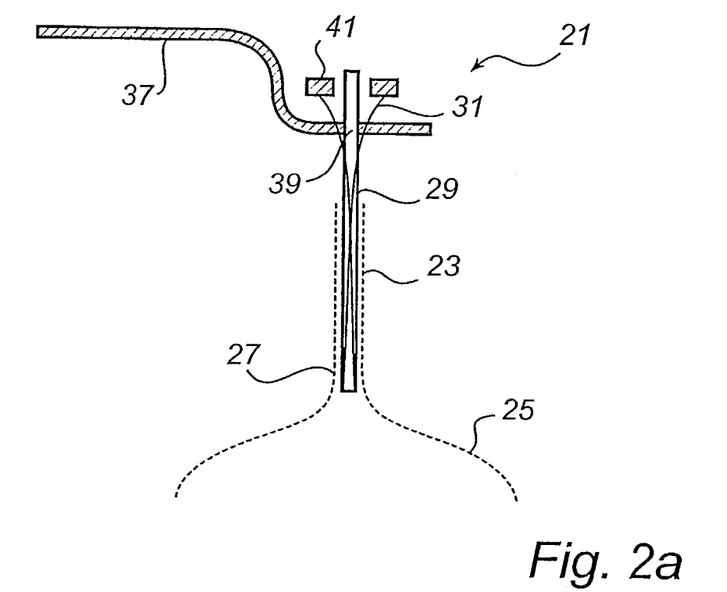
FIGS. 2a and 2b illustrate schematically an arrangement according to the present invention, in a preferred application.
Figure 2B:
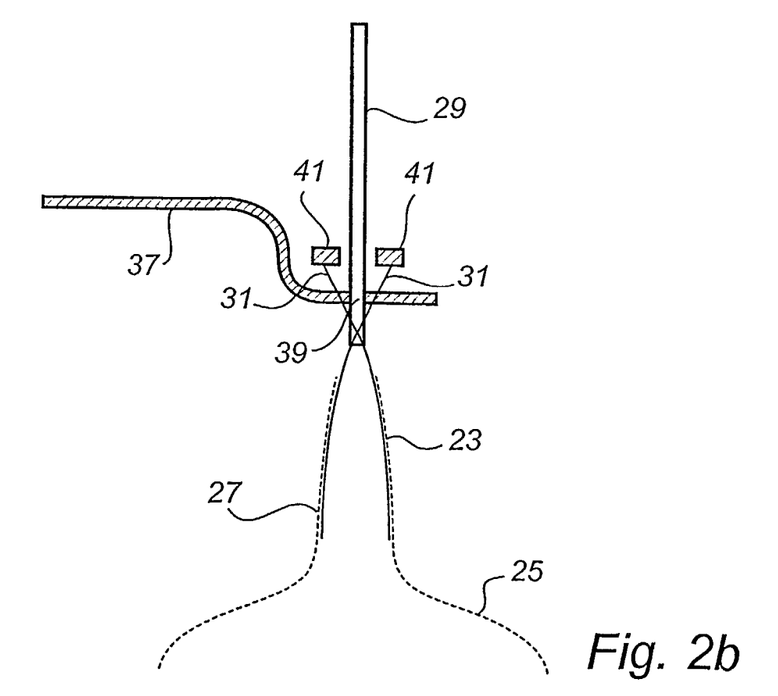

FIGS. 2a and 2b show schematically an arrangement 21 according to the present invention, in a preferred application, namely that of treating female urinary incontinence. Thus, the figures show (with dotted lines) female urinary organs including a urethra 23 and a urinary bladder 25. The inner or distal third part of the urethra 23, i.e. the part closest to the urinary bladder 25, has muscles for preventing urinary leakage. These muscles are also called the functional sphincter 27. When a person is incontinent, the cause is often a slack functional sphincter 27 which does not seal the urethra 23 properly. It is therefore good advice to inject a reinforcing bulking agent.

Accordingly, as shown in FIG. 2a an arrangement 21 according to the invention is used for injecting the bulking agent. The arrangement comprises a tubular sheath 29 which has received two elongate structural elements or, in this case, injection needles 31. Even though only two needles 31 are shown for the purpose of clarity, it is obviously conceivable to use more. For instance, four needles has been found to be suitable in some cases. The structural elements are in FIG. 2a, just like in FIG. 1a, received in the lumen through later apertures (not shown) in the sheath wall. Also, the needles 31 have a similar crosswise configuration as in FIG. 1a, which is particularly favourable for this illustrated application. In order to facilitate the handling of the arrangement, a sheath holder 37 is also provided. The sheath holder 37 has a central hole 39, through which the sheath 29 extends. The hole 39 allows the sheath 29 to be advanced and retracted in the longitudinal direction of the sheath 29. The sheath holder 37 is also provided with two channels (not shown) for guiding the respective injection needle 31 in a direction toward the geometrical central longitudinal axis of the sheath 29.

The injecting procedure is thus started by entering the sheath 29, together with the injection needles 31, into the urethra 23 and advancing them towards the urinary bladder 25. The injection needles 31 are during this advancement kept in an enclosed position, corresponding to that shown in FIG. 1a, inside the sheath 29. When the open distal end of the sheath 29 reaches the point of leakage of the functional sphincter 27, urine begins to drip or flow through the lumen of the sheath 29 and is detected at the proximal end of the sheath 29. This means that the arrangement 21 is already in place at the desired injection site, and no adjustment in the longitudinal direction is necessary.

Subsequently, when the urine is detected, the sheath 29 is retracted proximally to the position shown in FIG. 2b. The injection needles 31 are thereby uncovered and, due to their biased state, they will strive to deflect radially away from the central longitudinal axis of the sheath 29. The needles 31 will get into touch with the mucous member of the functional sphincter 27 and because of their inherent outwardly directed radial force, they will smooth out and distend the mucous member. This is shown in FIG. 2b. Because the mucous member has been smoothened out it can now easily be penetrated by the needles 31. The needles 31 are slightly retracted so as to get an angle of penetration and are then driven forward into the body tissue, after which the bulking agent is injected by means of the needles 31. The needles 31 are provided with some sort of conventional injection mechanism 41. Afterwards, by pushing the sheath 29 forward distally, the needles 31 will yet again be covered and can be taken out of the body cavity without damaging the tissue. Alternatively, the sheath 29 and the shielded needles 31 are moved a short distance to a new injection site.

The arrangement 21 is suitably assembled by first driving the sheath 29 through the hole 39 of the sheath holder 37. Then the injection needles 31 are driven through the channels of the sheath holder 37 and caused to enter the lumen of the sheath 29 through the lateral apertures.

The needles are preferably symmetrically arranged and evenly spaced, however they may have asymmetrical configurations as well, as long as the mucous member is adequately distended and the needles access the accurate injection site.

It should also be noted that in FIGS. 2a and 2b the needles 31 are essentially in a fixed position relative to the sheath holder 37. In other words the needles 31 are essentially immovable in the longitudinal direction as the sheath 29 is retracted. However, they are subject to a distinct radial or angular motion.

It should further be noted that each needle 31 is in a way "fixed" to the respective aperture. In other words, while the sheath 29 is retracted from the first shielding position to the second exposing position, it is essentially the same spot on the needle 31 that is to be found in the actual aperture. However, in the first position, said spot essentially abuts the proximal end of the aperture, and in the second position said spot essentially abuts the distal end of the aperture.

Figure 3A:
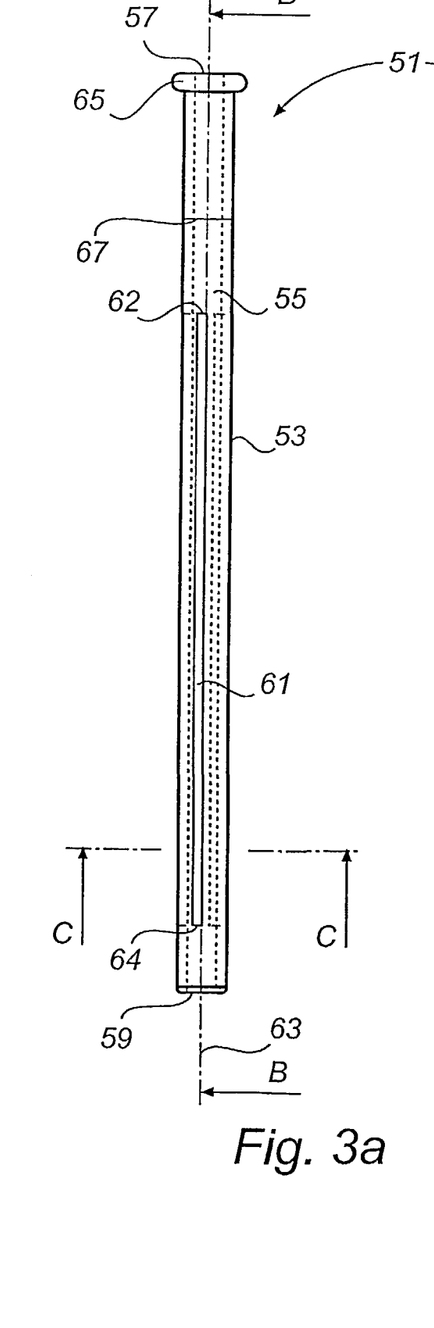
FIGS. 3a–3c illustrate schematically a sheath for use in an arrangement or method according to the present invention.
Figure 3B:
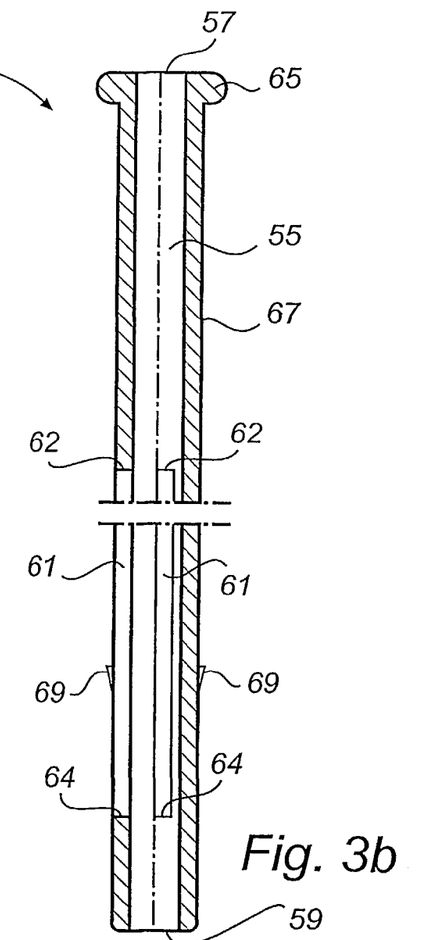
Figure 3C:
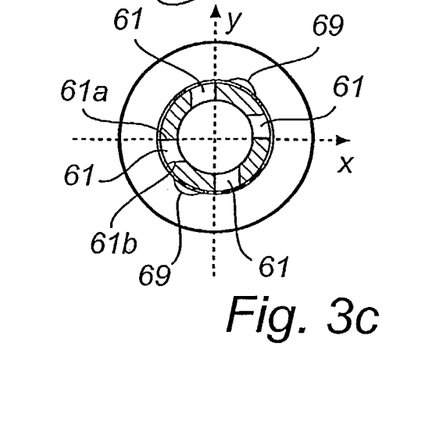

FIGS. 3a–3c illustrate schematically a sheath 51 for use in an arrangement or method according to the present invention. Note that the different figures are not true to scale in relation to each other.

FIG. 3a is a side view of the tubular sheath 51, which has a wall 53 defining an interior lumen 55. The sheath 51 has an open proximal end 57 and an open distal end 59. The sheath 51 has an approximate length of 120 mm. The wall 53 is provided with four apertures 61 (one shown) symmetrical spaced round the circumference of the wall 53. Each aperture 61 has the shape of an elongate slot which extends in parallel with the geometrical longitudinal axis 63 of the sheath 51, from about 9 mm of the distal end 59 to about 46 mm from the proximal end 57 of the sheath 51. The width of each aperture 61 should correspond to the diameter of an elongate structural element to be inserted. In the shown embodiment the width is about 1.2 mm.

FIG. 3b is a cross section of the sheath 51 taken along the central longitudinal axis 63 thereof, indicated by section B—B. The sheath 51 in this figure is shown with a middle portion cut away for the sake of clarity. As can be seen from this figure, the diameter of the sheath 51 is not constant. The diameter is 6.0 mm from the distal end 59 and all the way to about 91.2 mm proximally of the distal end 59. After that there is an increased diameter of 6.3 mm for about 26 mm, and the last 2 mm, serving as a gripping means 65 with rounded out periphery, has a diameter of 10 mm. The sheath holder (shown in FIGS. 4a–4c) has a hole for receiving the sheath 51. For a sheath 51 according to FIGS. 3a–3c, the hole of a matching sheath holder has a diameter of about 6 mm. Thus, this allows for the distal end 59 of the sheath 51 to be inserted in the hole and the sheath 51 may be advanced. However, the slight increase from 6.0 mm to 6.3 mm is enough to prevent the sheath 51 from being advanced to far distally. Said slightly enlarged diameter of the sheath 51 thus provides an annular stop lug 67. Another stopping arrangement is provided about 19 mm from the distal end 59 of the sheath 51. It comprises two barbs 69, preferably somewhat flexible, which allow the sheath 51 to be advanced through the hole of the sheath holder. Once the barbs 69 have been passed through the hole, the sheath 51 is prevented from being retracted to far, since the proximal surface of the barbs 69 will abut against the sheath holder. Apart from these physical stops, i.e. the annular stop lug 67 and the distal barbs 69, the mobility of the sheath 51 is further limited by the length of the slot-shaped apertures 61 (two shown in FIG. 2b). The length of the apertures 61 sets the practical sliding range of the sheath 51, since each inserted elongate structural element will come into contact with the ends 62, 64 of the respective aperture 61.

FIG. 3b also shows that the lumen 55 of the sheath 51 is continuous, like a through hole or through bore. Since the lumen 55 extends from the open distal end 59 to the open proximal end 57 of the sheath 51, excellent fluid communication possibilities are enabled. This is particularly advantageous for detecting urine, as has previously been described. The lumen 55 has a diameter of approximately 4 mm.

FIG. 3c is a cross sectional view looking in the longitudinal direction of the sheath 51, taken along line C—C. For the sake of understanding a geometrical x-axis and a geometrical y-axis has been added in the figure. In this figure the four apertures 61 are clearly distinguished. As can be seen, each aperture 61 has a first side 61a extending radially which is centred, i.e. aligned along the x-axis and y-axis, respectively. Each aperture also have a second side 61b in parallel with and opposed to the first side 61a. The second side 61b is placed left of the first side 61a when seen from the centre of the lumen. This has the effect that the apertures 61 will be somewhat offset from the x-axis and y-axis, respectively. Since no two apertures 61 are arranged exactly opposite to one another, the elongate structural elements that are inserted are prevented from obstructing each other or becoming tangled. In FIG. 3c the two barbs 69 are also shown. They are located opposite each other and diagonally to the x- and y-axis.

Figures 4A, 4B, 4C:
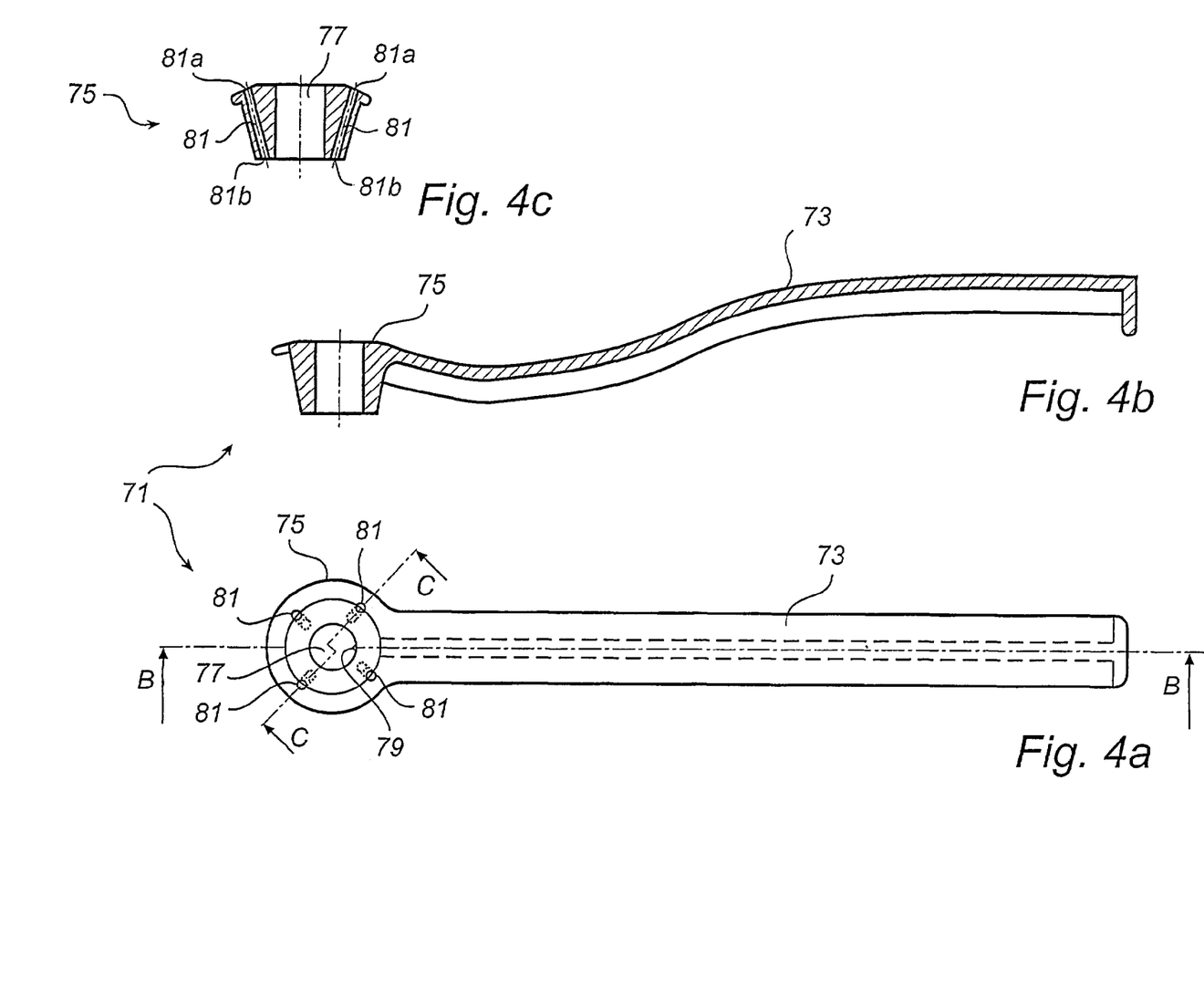
FIGS. 4a–4c illustrate schematically a sheath holder for use in an arrangement or method according to the present invention.

FIGS. 4a–4c illustrate schematically a sheath holder 71 for use in an arrangement and method according to the present invention.

FIG. 4a is a top view of the sheath holder 71. It comprises an elongated stem or handle portion 73 and a generally circular head or guiding portion 75. The handle portion 73 should be easy to grip and is about 100 mm long. The guiding portion 75 is provided with a central hole 77 having a diameter of 6.0–6.5 mm for guiding a sheath according to the invention. A triangular portion 79 is shown protruding 0.5 mm into the hole 77. This triangular portion 79 has the purpose of facilitating the guiding of the sheath and preventing the sheath from rotating. Thus, the distance between the tip of the triangular portion 79 and the other side of the hole 77 is 6.0 mm, and is adapted for a sheath like the one shown in FIGS. 3a–3c.

Continuing with FIG. 4a, circumferentially of said hole 77, four evenly spaced channels 81 are provided for guiding a respective elongate structural element. Each channel 81 has a diameter, e.g. 1.2 mm, which corresponds to the diameter of the respective structure element to be inserted. The channels 81 are angled (approximately 15°) with respect to the hole 77, the proximal top entrance 81a of each channel 81 being further away from the hole 77 than the distal bottom exit 81b. This is shown more clearly in FIG. 4c, which is a cross section taken across the guiding portion 75 and through the hole 77, as indicated by C—C in FIG. 4a. Even though four channels 81 are shown, other number may be provided. E.g. it may be sufficient with two or three, or it may be desired to have many more, e.g. twelve. Furthermore, the channels 81 do not have to be symmetrically arranged around the hole 77.

FIG. 4b is a cross section taken centrally along the length of the sheath holder 71, indicated by B—B. The figure shows that the sheath holder 71 has a curved handle portion 73 for facilitating gripping.

Figure 5:
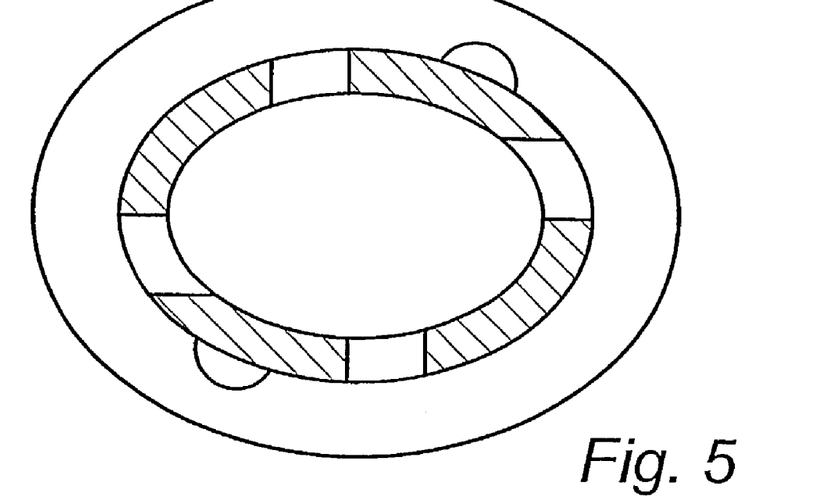
FIG. 5 illustrate schematically an example of a possible cross section of a sheath according to the present invention.

FIG. 5 illustrates schematically an example of a possible alternative cross section of a sheath according to the present invention. The cross sections is taken transversely of the sheath, i.e. perpendicularly to the longitudinal axis thereof, similarly to FIG. 3c. The previously discussed FIG. 3c illustrates a standard circular cross section of a tubular sheath, which e.g. is suitable for use in cavities, such as the urethra, having similar cross section. FIG. 5, however, illustrates an elliptical cross section of a tubular sheath. This would for instance be suitable for accessing the vocal cords, or other similarly shaped space. There are of course a great number of other possible alternatives, the cross section preferably being chosen in accordance with the specific application.

Figure 6:
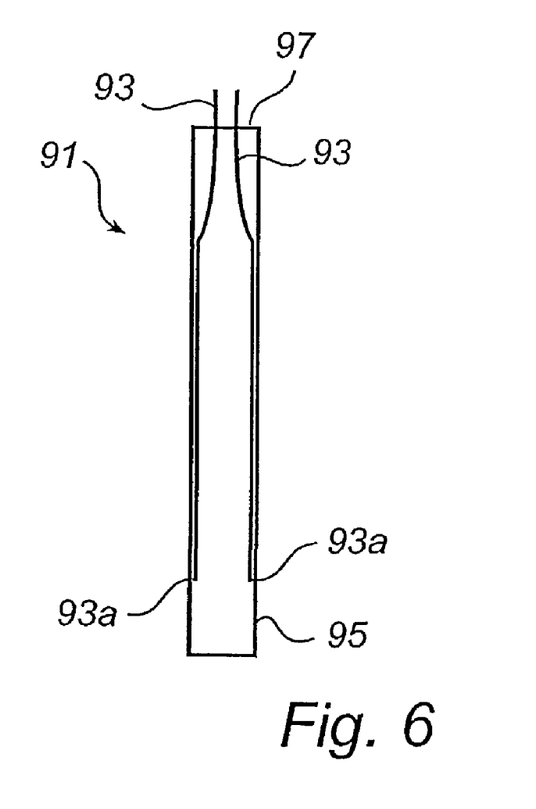
FIG. 6 illustrates schematically an alternative embodiment of an arrangement according to the present invention.

FIG. 6 illustrates schematically an alternative embodiment of an arrangement 91 according to the present invention. Instead of the previously shown crosswise configuration of the elongate structural elements, the structural elements 93, in this embodiment extend generally in parallel with each other. The elongate structural elements 93 are inserted through apertures (not shown) in the proximal end 97 of the sheath 95, instead of through lateral apertures, and do therefore not cross each other. However, they could be arranged to cross each other. A large distal part of each structural element 93 is somewhat curved. As each structural element is inserted with the distal end 93a curving away from the central longitudinal axis of the sheath, the distal end 93a will be pressed against the sheath wall, wherein each structural element 93 will become biased, striving to deflect radially away from the longitudinal axis. Thus, when the particular body organ is to be accessed, the structural elements 93 are displaced relative to the sheath 95, thereby activating the desired radial springing out of the structural elements 93.

It should be noted that numerous modifications and variations can be made without departing from the scope of the present invention defined in the accompanied claims.

Thus, it is to be understood that even though some specific embodiments and configurations have illustrated, they are primarily elucidative examples for the ease of understanding. Obviously, many others are conceivable.

Also, even if the previous description has stated certain dimensions, others are possible and may even be more suitable depending on what body organ is to be accessed and for what specific purpose.

The invention claimed is:

1. An arrangement to be passed through a body cavity for interacting with an internal body organ, comprising:
   an elongate sheath having at least one interior passage, said sheath having a proximal end and a distal end, said distal end being open and in communication with said at least one passage; and
   at least two elongate structural elements, each structural element having a proximal end and a distal end; wherein
   the structural elements are inserted in said at least one passage so that at least a distal portion of each element extends therethrough in the longitudinal direction of the sheath; wherein
   the structural elements are arranged to be displaced relative to the sheath from a first position, in which the distal end of each structural element is located inside said at least one passage and in which the arrangement is intended to be passed through a body cavity, to a second position, in which a distal portion of each structural element extends through the open distal end of the sheath and at least partly in the transverse direction away from the sheath for distending and/or expanding interaction between the distal end of each structural element and a body organ approached by the arrangement through a body cavity.

2. The arrangement as claimed in claim 1, wherein the sheath is tubular and has a lumen as said at least one passage.

3. The arrangement as claimed in claim 1, wherein each elongate structural element is tubular.

4. The arrangement as claimed in claim 3, wherein each elongate structural element is tubular in the form of a cannula.

5. The arrangement as claimed in claim 3, wherein each elongate structural element is in the form of an injection needle for injecting a substance into said body organ.

6. The arrangement as claimed in claim 1, wherein said elongate structural elements are mechanically biased in said first position and strive to deflect past the circumference of the sheath in the transverse direction thereof so that the structural elements reach said second position when being displaced relative the sheath through the open distal end thereof.

7. The arrangement as claimed in claim 1, wherein, in said second position, the distal end of each structural element is located beyond the transverse extent of the sheath.

8. The arrangement as claimed in claim 1, wherein, in said first position, the sheath is arranged to be proximally retracted relative to the structural elements so that they will have said second position.

9. The arrangement as claimed in claim 1, wherein said sheath is provided with at least one lateral aperture through which said elongate structural elements are inserted into said at least one passage.

10. The arrangement as claimed in claim 9, wherein said at least one lateral aperture is shaped as a slot extending generally in the longitudinal direction of the sheath, wherein the transverse dimension of said slot essentially corresponds to the transverse dimension of a structural element inserted therethrough so that the structural element can be displaced along the length of the slot.

11. The arrangement as claimed in claim 10, wherein the structural element abuts against the distal end of the slot when the structural element is in said second position.

12. The arrangement as claimed in claim 9, wherein a plurality of lateral apertures are circumferentially spaced round the sheath, and wherein at least two of the elongate structural elements, being received through different apertures, intersect each other crosswise in said at least one passage.

13. The arrangement as claimed in claim 1, wherein the proximal end of the sheath is open and said at least one passage extends between the proximal end and the distal end of the sheath, thereby allowing fluid communication between the two ends via said at least one passage.

14. The arrangement as claimed in claim 1, wherein the transverse dimension of said at least one passage essentially corresponds to the total transverse dimension of the inserted structural elements.

15. The arrangement as claimed in claim 1, further comprising a sheath holder for holding and guiding the sheath in the longitudinal direction of the sheath.

16. The arrangement as claimed in claim 15, wherein said sheath holder has a hole having a transverse dimension which substantially corresponds to the transverse dimension of the sheath, wherein said sheath is allowed to be at least partially passed through said hole.

17. The arrangement as claimed in claim 15, wherein a proximal stop is provided on the outside of the sheath, at a proximal portion thereof, for interaction with the sheath holder so as to limit distal advancement of the sheath relative to the sheath holder.

18. The arrangement as claimed in claim 15, wherein a distal stop is provided on the outside of the sheath for interaction with the sheath holder so as to limit proximal retraction of the sheath relative to the sheath holder.

19. The arrangement as claimed in claim 15, wherein said sheath holder is further arranged to guide and align said elongate structural elements in a direction towards said at least one passage.

20. The arrangement as claimed in claim 19, wherein said sheath holder has a channel for each structural element, the transverse dimension of each channel essentially corresponding to the transverse dimension of the structural element inserted in said channel, wherein each structural element extends at least from said channel, through said aperture in the sheath, and into said at least one passage.

21. The arrangement as claimed in claim 20, wherein said channels are located radially externally to said hole and extend generally in the longitudinal direction of the sheath.

22. The arrangement as claimed in claim 20, wherein the channels are straight and have an angle of inclination relative to the longitudinal direction of the sheath, such that the channels converge distally.

23. The arrangement as claimed in claim 20, wherein the channels have an elongate slit-shaped cross section perpendicular to the longitudinal direction of the sheath allowing the structural elements to be arranged with different angles of inclination.

24. The arrangement as claimed in claim 19, wherein the sheath holder is arranged for keeping the elongate structural elements unmoved relative to the sheath holder, when the sheath is retracted relative to the sheath holder.

25. The arrangement as claimed in claim 1, wherein at least a portion of each elongate structural element is flexible.

26. The arrangement as claimed in claim 1, wherein the elongate structural elements are circumferentially distributed, in relation to the sheath.

27. The arrangement as claimed in claim 1, wherein at least one of said elongate structural elements includes information transfer means.

28. A method for interacting with an internal body organ through a body cavity, comprising the steps of:
- providing an elongate tubular sheath having at least one interior passage, said sheath having a proximal end and a distal end, said distal end being open and in communication with said at least one passage;
- introducing at least two elongate structural elements in said at least one passage so that at least a distal portion of each element extends through said at least one passage in the longitudinal direction of the sheath, each structural element having a distal end and a proximal end, and so that the distal end of each structural element is located inside said at least one passage;
- inserting the sheath and the structural elements into the body cavity;
- displacing the structural elements relative to the sheath through said open distal end of the sheath so as to expose the distal ends of each structural element; and
- bringing the distal end of each structural element in the transverse direction of and away from the sheath so that the distal end of each structural element interacts with the body organ in a distending and/or expanding manner.

29. The method as claimed in claim 28, wherein a tubular sheath is used having a lumen as said at least one passage.

30. The method as claimed in claim 28, wherein tubular elongate structural elements are used.

31. The method as claimed in claim 30, wherein the tubular elongate structural elements are in the form of a cannula.

32. The method as claimed in claim 30, wherein the tubular elongate structural elements are in the form of an injection needle for injecting a substance into said body organ.

33. The method as claimed in claim 28, wherein said elongate structural elements are brought to a mechanically biased state when the distal ends are inside said lumen so that they strive to deflect past the circumference of the sheath in the transverse direction thereof, wherein a deflection follows automatically after the exposure of the distal ends of the structural elements as they are displaced through the opening.

34. The method as claimed in claim 28, wherein said step of relatively displacing includes proximally retracting the sheath so as to expose the distal ends of the structural elements.

35. The method as claimed in claim 28, wherein said step of inserting includes distally advancing the sheath and the structural elements until fluid, entering said at least one passage through the open distal end of the sheath from said body cavity, is detected.

36. The method as claimed in claim 35, wherein the fluid is detected at the proximal end of the sheath, said proximal end being open and in communication with said at least one passage.

37. The method as claimed in claim 28, wherein said distending and/or expanding is followed by a step of injecting a medical agent through said elongate structural elements into the body organ.

38. The method as claimed in claim 28, wherein said elongate structural elements are introduced laterally into said at least one passage.

39. The method as claimed in claim 38, wherein said elongate structural elements are circumferentially distributed in relation to the sheath so that the introduced elongate structural elements intersect each other, in said at least one passage.

40. An elongate tubular sheath for use in an arrangement as claimed in claim 1, said sheath having:
- a wall defining an interior lumen;
- at least one aperture in the wall, for allowing elongate structural elements to be inserted in said lumen so that at least a distal portion of each element extends through the lumen in the longitudinal direction of the sheath; and
- an open distal end in communication with said lumen for allowing the distal end of each structural element to protrude therethrough.

41. The sheath as claimed in claim 40, wherein said at least one aperture is laterally located in the wall, said aperture being shaped as a slot extending generally in the longitudinal direction of the sheath, the transverse dimension of said slot essentially corresponding to the transverse dimension of the structural element to be introduced.

42. The sheath as claimed in claim 40, wherein the sheath has an open proximal end in communication with said lumen.

43. Use of an arrangement as claimed in claim 1 for injecting a substance into the tissue of an internal body organ.

* * * * *